United States Patent
Phillips (10) Patent No.: US 10,098,740 B2
(45) Date of Patent: Oct. 16, 2018

(54) VENOUS VALVE PROSTHESES

(71) Applicant: Covidien LP, Mansfield, MA (US)

(72) Inventor: Shawn Phillips, Belle Plaine, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/211,868

(22) Filed: Jul. 15, 2016

(65) Prior Publication Data

US 2018/0014935 A1 Jan. 18, 2018

(51) Int. Cl.
*A61F 2/24* (2006.01)
*A61F 2/844* (2013.01)
*A61F 2/90* (2013.01)

(52) U.S. Cl.
CPC .......... *A61F 2/2475* (2013.01); *A61F 2/2436* (2013.01); *A61F 2/844* (2013.01); *A61F 2/90* (2013.01); *A61F 2210/0014* (2013.01)

(58) Field of Classification Search
CPC ............ A61F 2/2475; A61F 2220/0008; A61F 2230/0008; A61F 2210/0014; A61F 2230/0069; A61F 2/844; A61F 2/2436
See application file for complete search history.

(56) References Cited

U.S. PATENT DOCUMENTS

| 7,678,144 | B2 | 3/2010 | Bailey et al. |
| 2001/0011187 | A1 | 8/2001 | Pavcnik et al. |
| 2005/0240280 | A1* | 10/2005 | Aliski ................. A61F 2/04 623/23.68 |
| 2006/0282157 | A1* | 12/2006 | Hill ................. A61F 2/2418 623/1.24 |
| 2010/0082094 | A1* | 4/2010 | Quadri ................. A61F 2/2412 623/1.26 |
| 2010/0217385 | A1 | 8/2010 | Thompson et al. |
| 2015/0209146 | A1 | 7/2015 | Hill et al. |

(Continued)

FOREIGN PATENT DOCUMENTS

EP 1900343 10/2015
WO 03/011179 A2 2/2003

(Continued)

OTHER PUBLICATIONS

EP17180531.0, Extended European Search Report, dated Sep. 15, 2017, 8pgs.

(Continued)

*Primary Examiner* — Paul Prebilic
(74) *Attorney, Agent, or Firm* — Shumaker & Sieffert, P.A.

(57) ABSTRACT

In some examples an implantable medical device may include a frame and a flexible tubular valve body. The frame may define a frame lumen and may be expandable from a compressed configuration to an expanded configuration. The flexible tubular valve body may extend between a downstream end and an upstream end. The valve body may define a valve lumen, a downstream opening at the downstream end, and an upstream opening at the upstream end. The valve body may be attached to the frame such that the frame lumen is in fluid communication with the valve lumen. The valve body may comprise a neck and may be configured to fold about the neck to at least partially close the valve lumen. The valve body may be configured to collapse in an absence of fluid flow through the valve lumen to at least partially close the valve lumen.

32 Claims, 8 Drawing Sheets

(56) References Cited

U.S. PATENT DOCUMENTS

2016/0022421 A1  1/2016  Haverkost et al.
2017/0196692 A1* 7/2017  Kirk .................. A61F 2/915
2018/0078372 A1  3/2018  Hill et al.

FOREIGN PATENT DOCUMENTS

WO  2005/011535 A2  2/2005
WO  2010/129900 A1  11/2010

OTHER PUBLICATIONS

Pavcnik et al., "Percutaneous Management of Chronic Deep Venous Reflux: Review of Experimental Work and Early Clinical Experience With Bioprosthetic Valve," Vascular Medicine 2008; 13: 75-84, (Feb. 2008).

Tien et al., "Role of Sinus in Prosthetic Venous Valve," European Journal of Vascular and Endovascular Surgery, vol. 48, Issue 1, p. 98-104, Jul. 2014.

Us et al., "The Use of External Banding Increases the Durability of Transcommissural External Deep Venous Valve Repair," Eur J Vasc Endovasc Surg 33, 494-501 (2007),(Apr. 2007).

Pavcnik et al., "Percutaneous Autologous Venous Valve Transplantation: Short-Term Feasibility Study in an Ovine Model," Journal of Vascular Surgery, vol. 46, No. 2, pp. 338-345 (2007), (Aug. 2007).

* cited by examiner

VENOUS VALVE PROSTHESES

TECHNICAL FIELD

This disclosure relates to an implantable medical device, and more specifically to venous valve prostheses.

BACKGROUND

Venous valves are found within the vasculature of a mammal, particularly the veins. Venous valves prevent the backflow of blood during circulation. For example, venous valves help to fight backflow of blood in the legs caused by gravity pulling the blood away from the heart and back towards the feet of a person when standing. However, when venous valves fail to work properly, blood can flow backwards within the veins and pool in, for example, the legs. Such pooling of blood can cause the veins to become distended, thereby causing the venous valves to fail further. This progressively worsening disorder can lead to varicose veins and chronic venous insufficiency, which is painful and can lead to lower limb ulcerations.

Native venous valves are valves created by thin, overlapping leaflets of tissue that open in response to antegrade pressure, but close in response to retrograde pressure. These valves may be reconstructed in a surgical procedure, but are complicated to reconstruct. Known prosthetic venous valves that attempt to replicate the function of the native leaflet design are complicated to fabricate, may require extensive invasive surgery to implant, may be damaged if implanted by percutaneous delivery, and tend to form thrombosis soon after implementation.

SUMMARY

In some aspects, this disclosure describes example venous valve prostheses that are implantable medical devices. Each implantable medical device may include a frame defining a frame lumen and a valve body defining a valve lumen. The valve body may be connected to the frame such that the valve lumen is in fluid communication with the frame lumen. The frame may be expandable such that it may expand when deployed to a treatment area such that it may anchor the valve body within the treatment area which may be, for example, an area of a vein comprising a native venous valve. The valve body may comprise a neck and may be configured to fold about the neck to at least partially close the valve lumen in an absence of fluid flow through the valve lumen or in the presence of retrograde fluid flow, and to open in the presence of antegrade fluid flow through the valve lumen. The valve body may be further configured to collapse in the absence of fluid flow through the valve lumen to at least partially close the valve lumen.

In some examples, the implantable medical device may be delivered to a treatment site via a delivery catheter. A distal portion of the delivery catheter may be advanced to the treatment site and the implantable medical device may be deployed from the delivery catheter to the treatment site. In some examples, the treatment site may be an area of a vein, such as a vein within a leg of a patient, comprising a venous valve.

In general, in one aspect, the present disclosure describes an implantable medical device comprising a frame and a flexible tubular valve body. The frame defines a frame lumen and is expandable from a compressed configuration to an expanded configuration. The flexible tubular valve body extends between a downstream end and an upstream end. The valve body defines a valve lumen, a downstream opening at the downstream end, and an upstream opening at the upstream end. The valve body is attached to the frame such that the frame lumen is in fluid communication with the valve lumen. The valve body comprises a neck and is configured to fold about the neck to at least partially close the valve lumen in an absence of fluid flow through the valve lumen or in the presence of retrograde fluid flow, and the valve body is configured to open in the presence of antegrade fluid flow through the valve lumen. In some embodiments, the valve body is further configured to collapse in an absence of fluid flow through the valve lumen to at least partially close the valve lumen.

In various embodiments of the implantable medical device, the downstream opening is smaller than the upstream opening.

In certain embodiments of the implantable medical device, the downstream opening is circular. In certain other embodiments, the downstream opening is oval.

In various embodiments of the implantable medical device, a downstream portion of the valve body defines at least one crease such that the valve body is configured to preferentially fold along the crease to at least partially close the valve lumen.

In various embodiments of the implantable medical device, the valve lumen decreases in diameter as it extends away from the frame. In certain embodiments, a thickness of a material forming the valve body is smaller at the neck than at least at one other portion of the valve body.

In certain embodiments of the implantable medical device, the frame comprises steel. In certain other embodiments, the frame comprises nitinol.

In certain embodiments of the implantable medical device, the frame defines a coil. In some other embodiments, the frame defines a latticed structure. In still other embodiments, the frame defines an open ring. In certain other embodiments, the frame defines a closed ring. In various embodiments, the frame may be a combination of these configurations.

In some embodiments, valve body defines a ribbed exterior surface. In some other embodiments, the valve body defines a substantially smooth exterior surface.

In various embodiments, the valve body comprises at least one of a polymer or a fluoropolymer.

In various embodiments of the implantable medical device, the size of the downstream opening is approximately 50%-90% the size of the upstream opening.

In general, in another aspect, the present disclosure describes a method comprising advancing a distal end of a catheter to a treatment site within a patient. An implantable medical device is disposed within the catheter. The method further comprises releasing the implantable medical device from the catheter at the treatment site. The implantable medical device comprises a frame and a flexible tubular valve body. The frame defines a frame lumen. The frame is expandable from a compressed configuration to an expanded configuration. The flexible tubular valve body extends between a downstream end and an upstream end. The valve body defines a valve lumen, a downstream opening at the downstream end, and an upstream opening at the upstream end. The valve body is attached to the frame such that the frame lumen is in fluid communication with the valve lumen. The valve body comprises a neck and is configured to fold about the neck to at least partially close the valve lumen in an absence of fluid flow through the valve lumen or in the presence of retrograde fluid, and the valve body is configured to open in the presence of antegrade fluid flow through the valve lumen. In certain embodiments, the valve body is further configured to collapse in the presence of retrograde fluid flow or in the absence of fluid flow through the valve lumen to at least partially close the valve lumen.

In some embodiments, the method further comprises inserting a guide member into a vasculature of the patient, and advancing the distal end of the catheter to the treatment site over the guide member.

In various embodiments, the treatment site comprises a native venous valve of the patient.

In certain embodiments, the downstream opening is smaller than the upstream opening.

In certain embodiments, the downstream opening is circular. In certain other embodiments, the downstream opening is oval.

In some embodiments, a downstream portion of the valve defines at least one crease, the valve body being configured to preferentially fold along the crease to at least partially close the valve lumen.

In various embodiments, the valve lumen decreases in diameter as it extends away from the frame.

In various embodiments, a thickness of a material forming the valve body is smaller at the neck than at least at one other portion of the valve body.

In certain embodiments, the frame comprises steel. In certain other embodiments, the frame comprises nitinol.

In certain embodiments, the frame defines a coil. In certain other embodiments, the frame defines a latticed structure. In certain other embodiments, the frame defines an open ring. In still other embodiments, the frame defines a closed ring. In various embodiments, the frame may be a combination of these configurations.

In some embodiments, the valve body defines a ribbed exterior surface. In certain other embodiments, the valve body defines a substantially smooth exterior surface.

In various embodiments, the valve body comprises at least one of a polymer or a fluoropolymer.

In various embodiments, the size of the downstream opening is approximately 50%-90% the size of the upstream opening.

In general, in yet another aspect, the disclosure describes an implantable medical device comprises a frame and a flexible tubular valve body. The frame defines a frame lumen. The frame is expandable from a compressed configuration to an expanded configuration. The flexible tubular valve body extends between a downstream end and an upstream end. The valve body defines a valve lumen, a downstream opening at the downstream end, and an upstream opening at the upstream end. The valve body is attached to the frame such that the frame lumen is in fluid communication with the valve lumen. The valve body comprises a neck and is configured to fold about the neck to at least partially close the valve lumen in an absence of fluid flow through the valve lumen or in the presence of retrograde fluid flow, and the valve body is configured to open in the presence of antegrade fluid flow through the valve lumen. In some embodiments, the valve body is further configured to collapse in an absence of fluid flow through the valve lumen to at least partially close the valve lumen. The downstream opening is smaller than the upstream opening.

In various embodiments, the frame comprises steel. In certain other embodiments, the frame comprises nitinol.

In various embodiments, the frame defines a coil. In some other embodiments, the frame defines a latticed structure. In certain other embodiments, the frame defines an open ring. In still other embodiments, the frame defines a closed ring. In various embodiments, the frame may be a combination of these configurations.

In various embodiments, the valve body defines a ribbed exterior surface. In some other embodiments, the valve body defines a substantially smooth exterior surface.

In various embodiments, the size of the downstream opening is approximately 50%-90% the size of the upstream opening.

In various embodiments, a downstream portion of the valve body defines at least one crease, the valve body being configured to preferentially fold along the crease to at least partially close the valve lumen.

In various embodiments, the valve lumen decreases in diameter as it extends away from the frame.

In certain embodiments, a thickness of a material forming the valve body is smaller at the neck than at least at one other portion of the valve body.

In various embodiments, the valve body comprises at least one of a polymer or a fluoropolymer.

The disclosure can be implemented to realize one or more of the following advantages. The implantable medical device may be delivered transluminally more easily than other implantable prosthetic venous valves, thereby also eliminating the need for extensive, open surgical procedures. The valve body may provide a more robust device that is easier to deliver transluminally compared to known prosthetic venous valves, especially known venous valves that attempt to replicate a leaf structure. The valve body is easier to fabricate than trying to replicate a native leaf structure. Further, the valve body has a more simple structure that helps alleviate the formation of thrombus. Further still, enabling transluminal delivery may reduce procedure time, virtually eliminated post-operative treatment and post-operative complications like infections, and helps recovery time.

The details of one or more aspects of the disclosure are set forth in the accompanying drawings and the description below. As used herein, downstream or antegrade means towards the heart of a patient (i.e., downstream fluid flow means blood flowing towards the heart), and upstream or retrograde means away from the heart of a patient (i.e., upstream fluid flow means blood flowing away from the heart). Other features, objects, and advantages of the techniques described in this disclosure will be apparent from the description and drawings, and from the claims.

DETAILED DESCRIPTION

In contrast to known prosthetic venous valves, the example venous valve prostheses described herein can be more easily delivered percutaneously, e.g., via a catheter percutaneously introduced into vasculature of a patient, without damage to the valve body. In addition, in some examples, the example venous valve prostheses described herein may help prevent thrombosis formation and be delivered to small veins.

In some examples, a venous valve prosthesis includes a frame defining a frame lumen and a valve body defining a valve lumen. The valve body may be connected to the frame such that the valve lumen is in fluid communication with the frame lumen and the frame may act as an anchor for the valve body to secure the valve body within a vein (or other vasculature). The frame may be expandable such that it may expand when deployed to a treatment area such that it may anchor the valve body within the treatment area which may be, for example, an area of a vein comprising a native venous valve or an area adjacent to a native venous valve. For example, the frame may be self-expanding (e.g., formed from a shape memory material) or may be expanded via a balloon or other mechanism. The valve body may comprise a neck and may be configured to fold about the neck to, for example, at least partially close the valve lumen and minimize or even prevent fluid flow through the valve lumen in an absence of fluid flow (i.e., when fluid flow is static). The valve body may be further configured to collapse in the presence of retrograde fluid flow to at least partially close the valve lumen, e.g., to minimize or even prevent fluid flow through the valve lumen in a retrograde direction. Further still, the valve body may be configured to open in the presence of antegrade fluid flow to enable the antegrade fluid flow through the valve lumen and thus past the venous valve prosthesis.

For example, the valve body may be configured to fold about the neck in the absence of fluid flow through the valve lumen (when fluid flow is static) and in a presence of retrograde fluid flow. In addition to, or instead of, folding about the neck in the absence of fluid flow through the valve lumen and in a presence of retrograde fluid flow, in some examples, the valve body may be configured to collapse in the presence of retrograde fluid flow, preventing flow through the valve lumen.

A valve body defining a valve lumen, and configured to fold about a neck and/or configured to collapse in an absence of fluid flow to at least partially close the valve lumen may enable opening of the valve lumen in the presence of antegrade fluid flow and closing of the valve lumen in the absence of fluid flow. This may enable passage of antegrade blood flow though the valve body and prevent retrograde blood flow though the valve body such that the valve body may function as a venous valve to aid in correct blood circulation through the vein or other vasculature. Because the valve body may also be configured to fold about the neck in a presence of retrograde fluid flow and the valve body may be further configured to collapse in the presence of retrograde fluid flow, this may further prevent retrograde blood flow through the vein, further facilitating desired blood flow though the vein. Thus, the venous valve prostheses may prevent retrograde blood flow within the veins and may thus prevent pooling of blood in, for example, the legs, thereby preventing distended veins, varicose veins, chronic venous insufficiency, and lower limb ulcerations.

In some examples, the venous valve prosthesis may be delivered to a treatment site via one or more catheters, which may be referred to herein as a delivery catheter. A distal portion of the catheter may be advanced to the treatment site and the venous valve prosthesis may be deployed from the delivery catheter to the treatment site. In some examples, the treatment site may be an area of a vein, such as a vein within a leg of a patient, comprising a native venous valve. The native venous valve may be, for example, not properly functioning, such that a clinician may determine that a venous valve prosthesis such as the ones described herein may help improve the patient's condition. In some examples, the treatment site may be adjacent to, downstream or upstream from a native venous valve. This implantation method may be simpler and less invasive than methods necessary to implant other types of venous valve prostheses, which may require additional implantation time, cost, pain, recovery, and risk.

In the figures below, the full length of the delivery catheter and/or guidewire is not shown. The length of the delivery catheter and/or guidewire can vary depending on the type of interventional procedure.

The venous valve prosthesis of the present disclosure may have particular application in a vein of a leg of a patient. However, the venous valve prosthesis may be used in any suitable location of the vasculature, or other hollow anatomical structures.

Figure 1A:
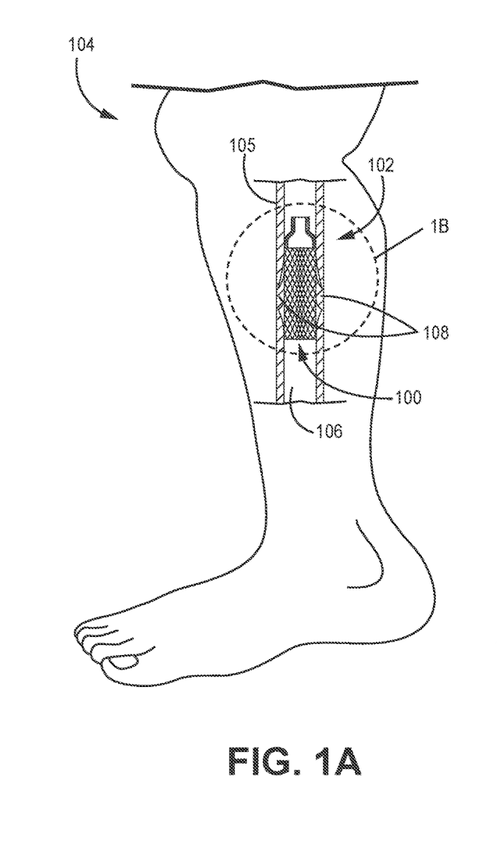
FIG. 1A is a cross-sectional view of an example venous valve prosthesis implanted within a vein of a leg of a patient.

FIG. 1A is a schematic cross-sectional view of an exemplary venous valve prosthesis 100 implanted within a vein 102 of a leg 104 of a patient. The vein 102 may include a vein wall 105 defining a vein lumen 106 and the venous valve prosthesis 100 may be implanted within the vein lumen 106. In the example shown in FIG. 1A, the venous valve prosthesis 100 is configured to function as a valve in place of a native venous valve 108 of the vein 102, where the native venous valve 108 may not be functioning properly. In the example shown in FIG. 1A, the venous valve prosthesis 100 is implanted to overlap with the native venous valve 108. The venous valve prosthesis 100 may push the native venous valve 108 up against the walls 105 of the vein 102. Although the figures show space between the native venous valve 108 and the walls 105 of the vein 102 and between the native venous valve 108, the venous valve prosthesis 100 may push the native venous valve 108 against the walls 105 of the vein 102 such that the venous valve prosthesis 100 lies substantially flat against the native venous valve 108 and such that the native venous valve 108 lies substantially flat against the walls 105. In some other examples, the venous valve prosthesis 100 may be implanted within the vein lumen 106 upstream or downstream of the native venous valve 106. The venous valve prosthesis 100 may be configured to enable antegrade blood flow through the venous valve prosthesis 100 to the heart of the patient and to prevent retrograde blood flow through the venous valve prosthesis 100 away from the heart. Components and functions of the venous valve prosthesis 100 are described in further detail below with reference to FIG. 1B. The venous valve prosthesis 100 may be implanted in a vein 102 or other vasculature of a patient of any suitable size. In some examples, the venous valve prosthesis 100 may be implanted in a vein 102 with a diameter of 5 mm to 12 mm.

Figure 1B:
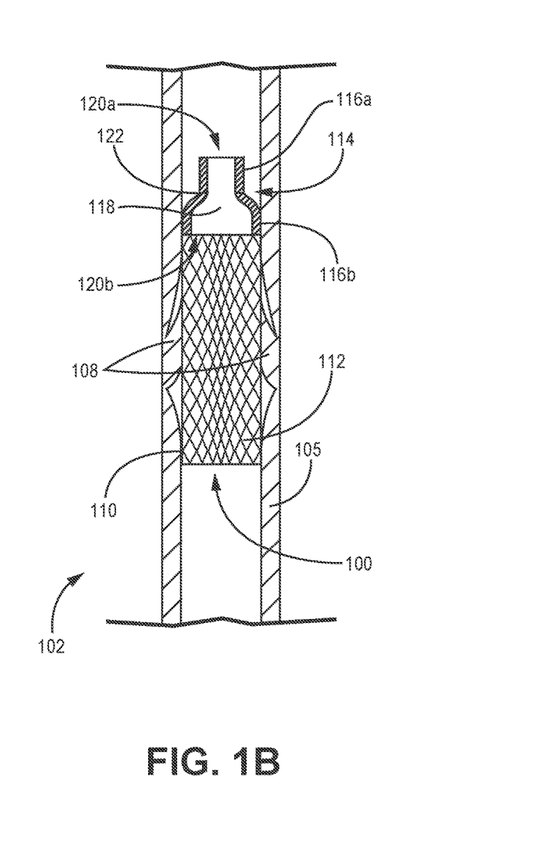
FIG. 1B is a cross-sectional view of the portion of FIG. 1A labeled 1B, showing the exemplary venous valve prosthesis of FIG. 1A implanted within a vein.

FIG. 1B is a schematic cross-sectional view of the portion of FIG. 1A labeled 1B, showing the venous valve prosthesis 100 of FIG. 1A implanted within the vein 102. In the example shown in FIG. 1B, the venous valve prosthesis 100 includes a frame 110 and a valve body 114, which may be a flexible tubular valve body.

The frame 110 may be expandable from a compressed configuration to an expanded configuration. In one example, the frame 110 may be self-expandable from the compressed configuration to the expanded configuration, e.g., without the aid of a balloon or other mechanism configured to apply an external force to the frame 110 to expand it. As another example, the frame 110 may be self-expandable from the compressed configuration to the expanded configuration via a balloon catheter introduced through a frame lumen 112 of the frame 110, or via another suitable technique.

In the example shown in FIG. 1B, the frame 110 is in an expanded configuration. The frame 110 may be configured to be able to expand further than shown in FIG. 1B, but further expansion of the frame 110 may be constrained by the wall 105 of the vein 102. The frame 110 may define the frame lumen 112 which may widen as the frame 110 expands. When the frame 110 is in an expanded configuration, as shown in FIG. 1B, the frame lumen 112 may enable fluid flow through the frame lumen 112. The frame 110 may be made of any suitable material. For example, the frame 110 may comprise steel. Alternatively or in addition, the frame 110 may comprise nitinol.

In the example shown in FIG. 1B, the frame 110 defines a latticed structure. For example, the frame 110 may be configured like a stent, e.g., the frame 110 may comprise a plurality of struts that are arranged and connected to provide the frame 110 with the desired structure, geometry, and mechanical characteristics (e.g., structural integrity and expansion characteristics). In some examples, the frame 110 may define a tubular structure having open cells or closed cells that facilitate expansion of the frame 110 and provide the frame 110 with the desired mechanical characteristics. The stent-like structure of the frame 110 in the example shown in FIG. 1B may provide additional benefits. For example, in addition to anchoring the valve body 114 within the vein 102, a frame 110 having a latticed structure, or another stent-like structure, may function as a stent to provide patency to the vein 102. In other examples, the frame 110 may define any suitable shape for securing the frame 110 and the valve body 114 within the vein 102.

In some examples, as in the illustrated example, the frame 110 may be configured to overlap and constrain the native venous valve 108 such that the native venous valve 108 does not obstruct blood flow or otherwise interfere with the functioning of the venous valve prosthesis 100. In other examples, the frame 110 may not be configured to overlap the native venous valve 108 or to otherwise interact with the native venous valve 108.

In the example shown in FIG. 1B, the valve body 114 may be flexible and tubular and may extend between a downstream end 116a and an upstream end 116b. The valve body 114 may define a valve lumen 118, a downstream opening 120a at the downstream end 116a, and an upstream opening 120b at the upstream end 116b. The valve body 114 may be attached to the frame 110 such that the frame lumen 112 is in fluid communication with the valve lumen 118 and the frame 110 may act as an anchor for the valve body 114 to secure the valve body 114 within the vein 102. For example, in the illustrated example, the upstream end 116b of the valve body 114 may be directly attached to the frame 110 or indirectly attached to the frame 110 via an intermediary structure positioned between the valve body 114 and the frame 110. In some examples, the downstream opening 120a of the valve body 114 may be smaller than the upstream opening 120b. For example, the size of the downstream opening 120a may be approximately 50%-90% of the size of the upstream opening 120b, such as about 80% of the size of the upstream opening 120b. The downstream opening 120a is selected to be large enough to prevent undue pooling of blood. In some examples, the valve lumen 118 may decrease in diameter as it extends away from the frame 110. For example, the valve lumen 118 may decrease in diameter from the upstream end 116a to a neck 122.

The valve body 114 may comprise a neck 122 and may be configured to fold about the neck 122. In some examples, the valve body 114 may be configured to fold about the neck 122 in an absence of fluid flow (when fluid flow is static) through the valve lumen 118. This folding about the neck 122 may cause at least a portion of the valve lumen 118 to close, thereby helping to prevent the flow of fluid through the valve body 114. In some examples, the valve body 114 may, in addition or alternatively, be configured to fold about the neck 122 in a presence of retrograde fluid flow, or configured to fold even further in the presence of retrograde fluid flow than in the presence of no fluid flow (when fluid flow is static). In some examples, the valve body 114 may be configured to unfold in a presence of antegrade fluid flow. This configuration of valve body 114 may enable passage of desired (antegrade) blood flow through the valve body 114 and restriction of undesired (retrograde) blood flow though the valve body 114 to facilitate desired (antegrade) blood flow though the vein 102 and desired blood circulation through the patient while also restricting retrograde flow that may result in blood pooling, vessel distention, and varicose veins, and additional adverse effects to patient.

The valve body 114 may also be configured to collapse in an absence of fluid flow through the valve lumen 118 to at least partially close the valve lumen 118. For example, in addition or alternatively to being configured to fold about the neck 122, the valve body 114 may be configured to retract in a radial direction such that at least a portion of valve lumen 118 is at least partially closed, e.g., partially closed or, in other examples, completely or substantially closed, such that no fluid or substantially no significant amount of fluid flows through the valve lumen 118 to one or both the downstream opening 116a and/or upstream end 116b.

In some examples, the valve body 114 may, in addition or alternatively, be configured to collapse in a presence of retrograde fluid flow. In some examples, the valve body 114 may be configured to expand to its normal configuration in a presence of antegrade flow, resulting in reopening of the valve lumen 118. This may enable passage of desired (antegrade) blood flow through valve body 114 and restriction of undesired (retrograde) blood flow though the valve body 114 to facilitate desired (antegrade) blood flow though the vein 102 and desired blood circulation through the patient.

The valve body 114 may comprise any suitable material. In some examples, the valve body 114 may comprise at least one of a polymer or a fluoropolymer. In some examples, the material composition and/or shape of the valve body 114 may facilitate the collapse and expansion of the valve body 114, as desired.

Figure 2A:
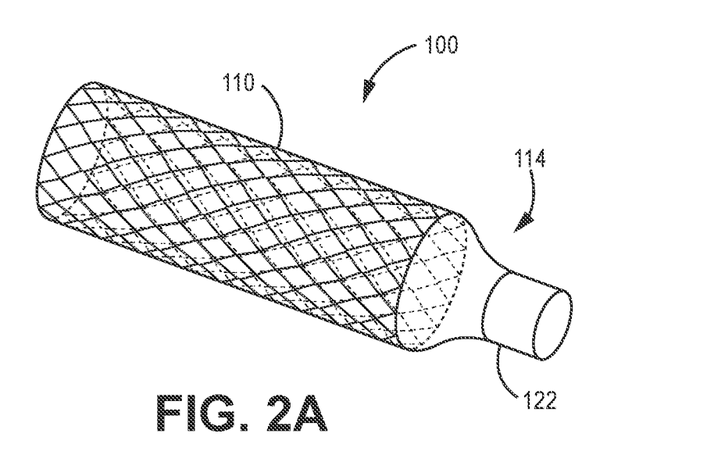
FIG. 2A is a perspective view of the exemplary venous valve prosthesis of FIGS. 1A and 1B showing the valve body in an unfolded configuration.
Figure 2B:
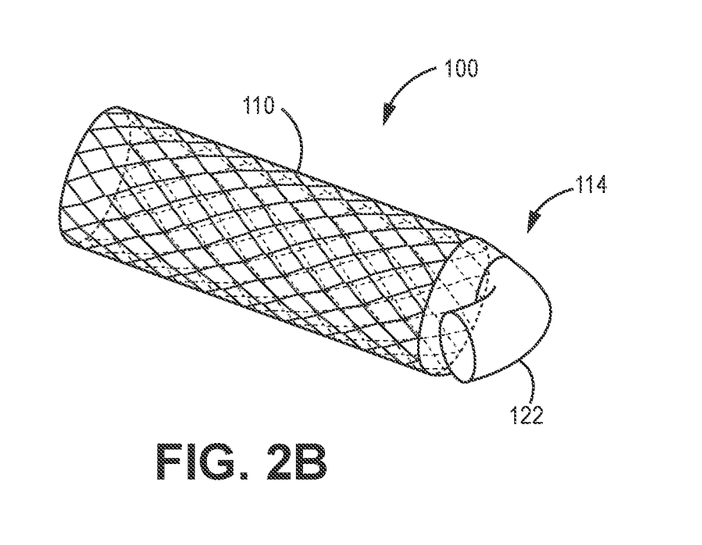
FIG. 2B is a perspective view of the exemplary venous valve prosthesis of FIGS. 1A and 1B showing the valve body in a folded configuration.

FIG. 2A is a perspective view of the exemplary venous valve prosthesis 100 of FIGS. 1A and 1B showing the valve body 114 in an unfolded configuration. FIG. 2B is a perspective view of the exemplary venous valve prosthesis 100 of FIGS. 1A, 1B, and 2A showing the valve body 114 in a folded configuration. As discussed above with reference to FIGS. 1A and 1B, the venous valve prosthesis 100 may include the frame 110 and the valve body 114. In the illustrated example, the frame 110 may define a latticed structure. In other examples, the frame 110 may define any suitable shape.

The valve body 114 may define the neck 122 and may be configured to fold about the neck 122, as shown in FIG. 2B. For example, the valve body 114 may be configured to fold about the neck 122 in an absence of fluid flow through valve lumen 118, shown in FIGS. 1A and 1B. This folding about the neck 122 may cause at least a portion of the valve lumen 118 to at least partially close and minimize, or even prevent, fluid flow through the valve lumen 118. In some examples, the valve body 114 may, in addition or alternatively, be configured to fold about the neck 122 in a presence of retrograde fluid flow. For example, in one embodiment, the valve body 114 maybe configured to fold about the neck 122 in the absence of fluid flow through valve lumen 118, thereby at least partially closing the valve lumen 118, and configured to fold further about the neck 122 in the presence of retrograde fluid flow to further close or completely close the valve lumen 118 to prevent retrograde fluid flow.

In some examples, valve body 114 may be configured to unfold in a presence of antegrade fluid flow, as shown in FIG. 1A. In still other embodiments, the valve body 114 maybe configured to unfold in the presence of antegrade fluid flow and in the absence of fluid flow through valve lumen 118, and configured to fold about the neck 122 in the presence of retrograde fluid flow.

This folding and unfolding of the valve body 114 about the neck 122 may enable passage of desired (antegrade) blood flow through the valve body 114 and restriction of undesired (retrograde) blood flow though the valve body 114 to facilitate desired (antegrade) blood flow though the vein 102 and desired blood circulation through the patient and may thus prevent pooling of blood and other undesirable effects.

The valve body 114 may be constructed in any suitable manner according to particular needs. In some examples, a thickness of a material forming the valve body 114 may be smaller at the neck 122 than at least at one other portion of the valve body 114. For example, a valve body 114 may be constructed of the same material but the material may be thinner at the neck 122 than at other portions of the valve body 114. This may facilitate bending of the valve body 114 at the neck 122 as the neck 122 may be more flexible than other portions of the valve body 114 due to the decreased thickness of the material at the neck 122.

As another example, the portion of the valve body 114 forming the neck 122 may be made of a different, more flexible, material than other portions of the valve body 114. This may also facilitate bending of the valve body 114 at the neck 122 as the neck 122 may be more flexible than other portions of the valve body 114 due to the more flexible material at the neck 122. As another example, supportive ribs may be provided at portions of the valve body 114 other than the neck 122 (see FIG. 4C, described further below), such that the neck 122 is more flexible that the ribbed portions and thus more able to bend than other portions of the valve body 114.

Figure 3A:
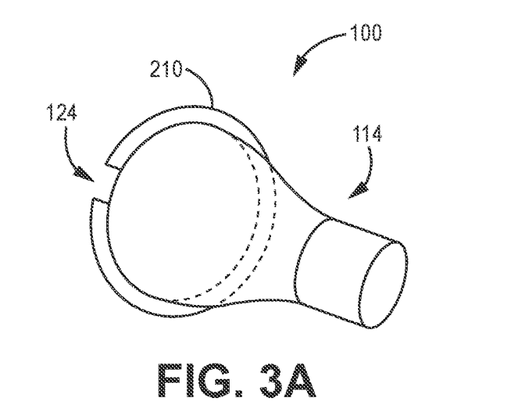
FIGS. 3A-3C are perspective views of other examples of venous valve prostheses.
Figure 3B:
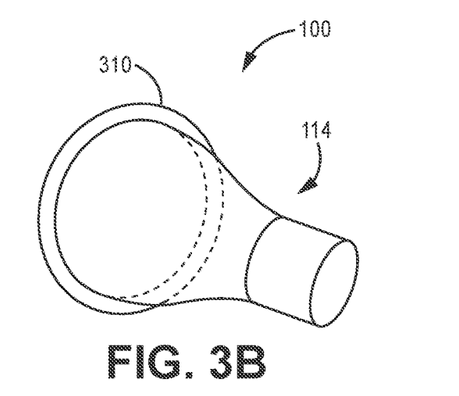
Figure 3C:
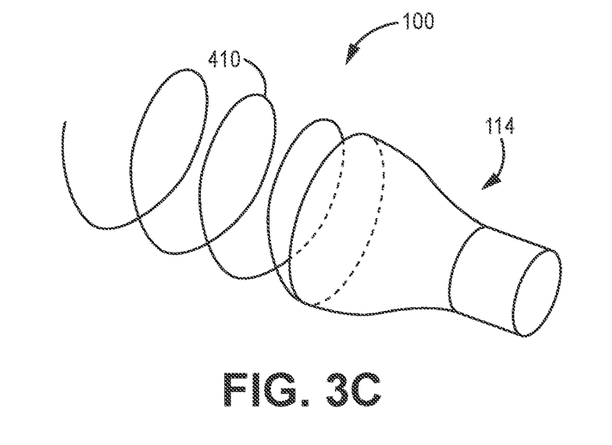

FIGS. 3A-3C are perspective views of other examples of venous valve prostheses 100. As described above with reference to FIGS. 1A-2B, the venous valve prosthesis 100 may include a frame 110 and a valve body 114. The frame 110 may have different shapes than the latticed structure illustrated in FIGS. 1A-2B.

For example, in the example illustrated in FIG. 3A, the venous valve prosthesis 100 may include a frame 210 and a valve body 114, where the frame 210 defines an open ring. The frame 210 may substantially form a ring shape but may define a gap 124 such that it does not define a complete ring. The frame 210 is configured to expand to engage wall 105 of the vein 102 (or other vasculature) in order to anchor the valve body 114 within the vein 102 (or other vasculature). The open ring structure of the frame 210 may enable the frame 210 to accommodate a range of different vein sizes. For example, the open ring structure may enable the frame 210 to expand or contract as needed to engage with different diameter veins.

In the example illustrated in FIG. 3B, the venous valve prosthesis 100 may include a frame 310 and the valve body 114. The frame 310 may define a closed ring. For example, the frame 310 may form a ring shape with no gaps. The frame 310 is expandable from a compressed state to an expanded state in which the frame 310 engages the wall 105 of the vein 102 (or other vasculature) in order to anchor the valve body 114 within the vein 102 (or other vasculature).

In the example illustrated in FIG. 3C, the venous valve prosthesis 100 may include a frame 410 and the valve body 114. The frame 410 may define a coil, which may exhibit spring-like characteristics. For example, the frame 410 may form a helical shape. The frame 410 is expandable from a compressed state to an expanded state in which the frame 410 engages the wall 105 of the vein 102 (or other vasculature) in order to anchor the valve body 114 within the vein 102 (or other vasculature). The coil structure of the frame 410 may enable the frame 210 to accommodate a range of different vein sizes. For example, similar to the open ring structure of the frame 210 (FIG. 3A), the coil structure of the frame 410 may enable the frame 410 to expand or contract as needed to engage with different diameter veins.

Although certain examples are illustrated, a frame 110 may define any suitable shape according to particular needs. The shapes described, including the latticed structure, the open ring, the closed ring, and the coil, may facilitate collapse of the frame 110, 210, 310, or 410, respectively, for delivery via a delivery catheter and may facilitate expansion of the frame 110, 210, 310, or 410, respectively, when delivered within the vein 102.

Figure 4A:
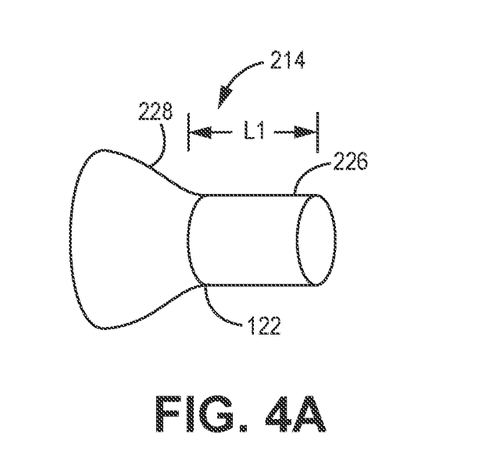
FIGS. 4A-4C are a perspective views of other examples of the valve body of the exemplary venous valve prostheses of FIGS. 1A-3C.
Figure 4B:
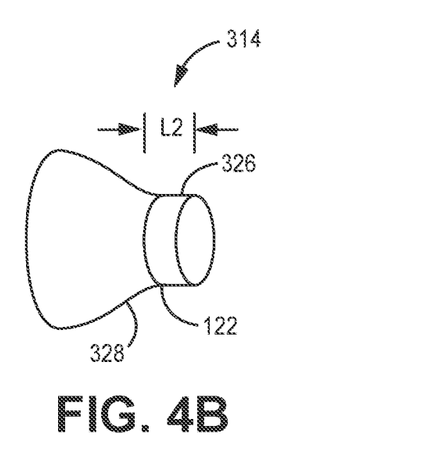
Figure 4C:
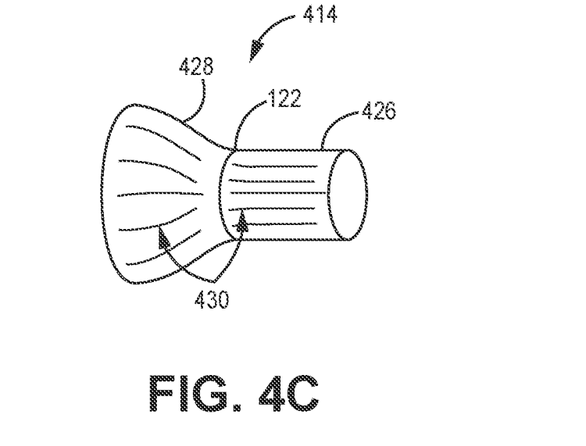

FIGS. 4A-4C are perspective views of other examples of the valve body 114 of the venous valve prosthesis 100.

As shown in FIG. 4A, a valve body 214 may include a downstream portion 226, which may be a portion of the valve body 214 downstream from the neck 122 when the valve body 214 is implanted in the vein 102 and having a length L1, and an upstream portion 228, which may be a portion of the valve body 214 upstream from neck 122 when the valve body 214 is implanted in the vein 102. As shown in FIG. 4B, a valve body 314 may include a downstream portion 326, which may be a portion of the valve body 314 downstream from the neck 122 when the valve body 314 is implanted in the vein 102 and having a length L2, and an upstream portion 328 which may be a portion of the valve body 314 upstream from the neck 122 when the valve body 314 is implanted in the vein 102. As shown in FIGS. 4A and 4B, the downstream portion 226 or 326 may have any suitable length. For example, the downstream portion 226 of valve body 214 may have a length L1 that may be relatively long, as shown in FIG. 4A, and the downstream portion 326 of the valve body 314 may have a length L2 that may be relatively short, as shown in FIG. 4B. In some examples, a longer downstream portion, such as the downstream portion 226 of the valve body 214 having length L1, may enable a larger folded portion and less force to fold when the valve body 214 folds about the neck 122 and therefore better obstruction of flow. In some examples, a shorter downstream portion, such as the downstream portion 326 of the valve body 314 having length L2, may provide a more compact design and less likely obstruction of desired, antegrade, blood flow. The length and other characteristics of the downstream portion 226 or 326, such as its diameter and material composition, may be adjusted accordingly according to particular needs.

In some examples, the valve body 114 may include a plurality of structural support members that help provide the valve body 114 with sufficient rigidity, for example, to help prevent the valve body 114 from inverting in the presence of back pressure on the valve body 114 (in a direction towards the frame 110, such as from retrograde fluid flow). For example, as shown in FIG. 4C, a valve body 414 may define a plurality of ribs 430 such that the valve body 414 defines a ribbed exterior surface. The ribs 430 may be configured to maintain structural integrity of the valve body 414. In some examples, the ribs 430 may extend along the length of the valve body 414. In other examples, a valve body may define a substantially smooth exterior surface. In other examples, the ribs 430 may be located on an interior surface of a valve body. In other examples, the ribs 430 may be located within the material of a valve body, between the inner and outer surfaces of the valve body, such that the ribs 430 are not visible on the exterior or interior surfaces of the valve body. In some examples, such as the example shown in FIG. 4C, the ribs 430 may be on portions of the valve body 414 other than the neck 122, including a downstream portion 426 and an upstream portion 428, and may not be on the neck 122. This may result in the neck 122 being more flexible than other portions of the valve body 414, which may facilitate folding of the valve body 414 about the neck 122.

Figure 5A:
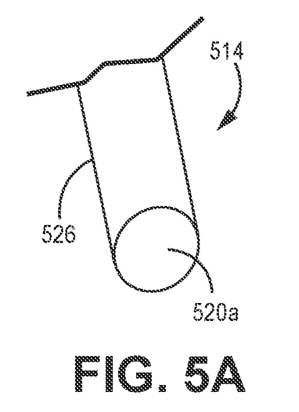
FIGS. 5A-5C are perspective views of examples of the downstream opening of the valve body of the exemplary venous valve prostheses of FIGS. 1A-4C.
Figure 5B:
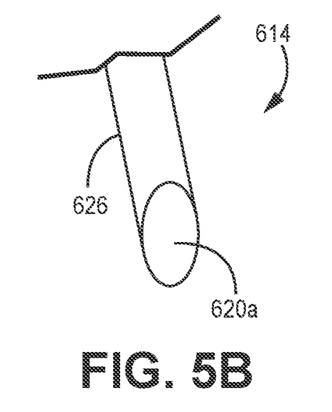
Figure 5C:
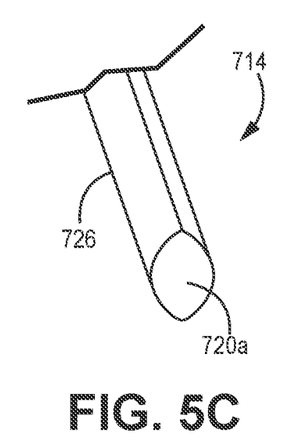

The valve body 114 may define a downstream opening 120a having any suitable shape. FIGS. 5A-5C are perspective views of several exemplary downstream openings 120a on a downstream portion of the valve body 114. FIG. 5A shows a downstream portion 526 of an example valve body 514. In the example illustrated in FIG. 5A, a downstream opening 520a may be substantially round. FIG. 5B shows a downstream portion 626 of an example valve body 614. In the example illustrated in FIG. 5B, a downstream opening 620a may be substantially oval. An oval downstream opening 620a may help facilitate closure of the downstream portion 626 of the valve body 614 in the absence of fluid flow through the valve body 614. For example, the oval opening may tend to collapse (e.g., such that the walls of the downstream portion 626 move inward towards a longitudinal center of the downstream portion 626) more quickly than the round opening 520a (FIG. 5A).

FIG. 5C shows a downstream portion 726 of an example valve body 714. In the example illustrated in FIG. 5C, the downstream portion 726 of the valve body 714 may define one or more creases. For example, in the example illustrated in FIG. 5C, the downstream portion 726 defines two creases on opposite sides of the downstream portion 726 such that the downstream opening 720a is in the shape of two half-moons joined at each end. This shape may facilitate collapse of the downstream portion 726 of the valve body 714 as the downstream portion 726 may fold relatively flat to collapse in the absence of antegrade fluid flow, in the presence of retrograde fluid flow, and/or when fluid flow is static. This may additionally facilitate folding of the valve body 714 about the neck 112. For example, the valve body 714 may more easily fold about the neck 122 when the downstream portion 726 is flattened. This may facilitate proper functioning of the venous valve prosthesis 100 and, thus, proper blood flow through the vein 102. This may prevent undesirable retrograde blood flow through the vein 102 and the resulting negative effects to the patient.

Figure 6A:
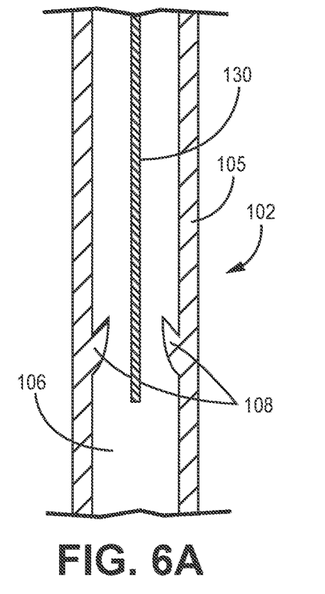
FIGS. 6A-6G are partial, cross-sectional views of a system including the exemplary venous valve prosthesis of FIGS. 1A-2B in various stages of use at a treatment site comprising a venous valve in a vein of a patient.

FIGS. 6A-6G are partial, cross-sectional views of a system including the venous valve prosthesis 100 of FIGS. 1A-2B in various stages of use at a treatment site comprising a native venous valve 108 in the vein 102 of the patient. The vein 102 may comprise a wall 105 defining the vein lumen 106. In the illustrated example, the venous valve prosthesis 100 may be implanted such that it at least partially overlaps with a native venous valve 108. In other examples, the treatment site may be located downstream or upstream of the native venous valve 108 or in any other suitable location, according to particular needs of the particular patient. FIG. 7 is a flowchart illustrating a method including the various stages of use of the system shown in FIGS. 6A-6G A guidewire 130 may be inserted into the vein 102 of a patient (FIG. 6A and 752 of FIG. 7). The guidewire 130 may be advanced through the vein lumen 106 of the vein 102 to position a leading end (distal end) of the guidewire 130 at a target location as determined by the clinician.

Figure 6B:
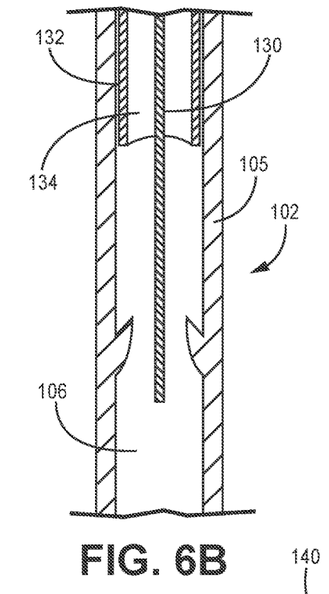
Figure 6C:
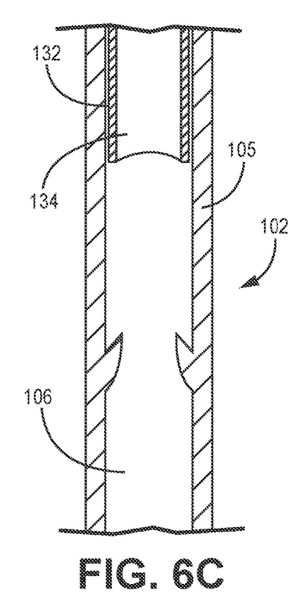
Figure 7:
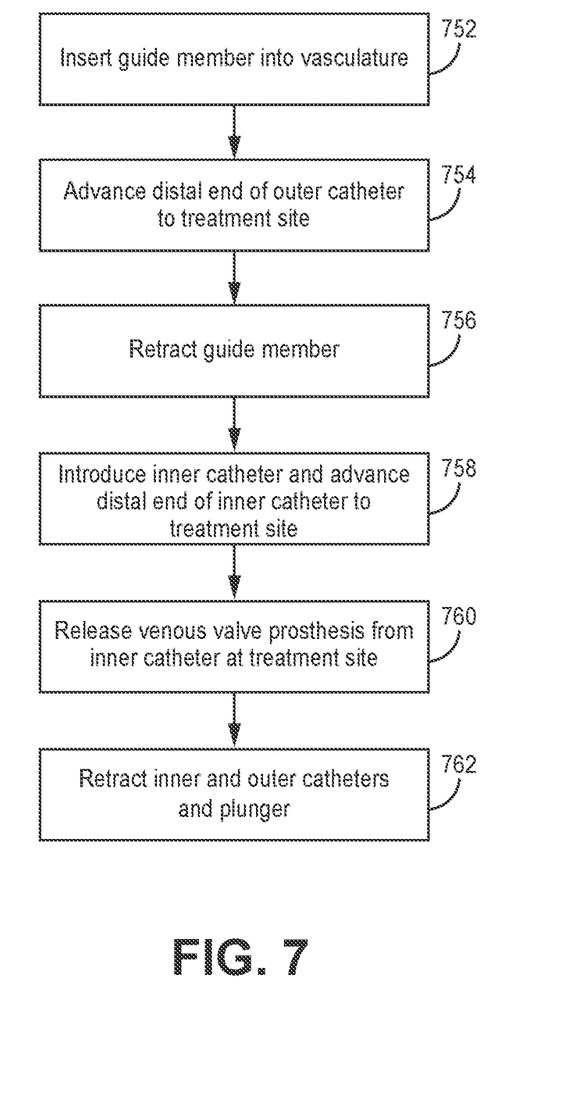
FIG. 7 is a flowchart illustrating a method including the various stages of use of the exemplary system shown in FIGS. 6A-6G.

An outer catheter 132 may be introduced over the guidewire 130 and a distal portion of the outer catheter 132 may be advanced substantially adjacent to a treatment site as determined by the clinician (FIG. 6B and 754 of FIG. 7). The outer catheter 132 may define an outer catheter lumen 134.

The guidewire 130 may be retracted to remove the guidewire 130 from the outer catheter lumen 134 (FIG. 6C and 756 of FIG. 7), while leaving the outer catheter 132 in place.

Figure 6D:
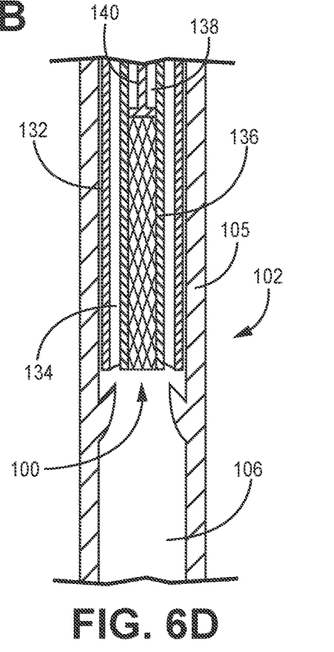

An inner catheter 136 may be introduced within the outer catheter 132 and a distal portion of inner catheter 136 may be advanced proximate to the treatment site (FIG. 6D and 758 of FIG. 7). In some examples, the distal portion of inner catheter 136 may be advanced to be substantially even with the distal portion of outer catheter 132. The inner catheter 136 may define an inner catheter lumen 138. A distal portion of the inner catheter lumen 138 may house the venous valve prosthesis 100. A plunger 140 may also be located in the inner catheter lumen 138, proximal of the venous valve prosthesis 100, and may be configured to help release the venous valve prosthesis 100 from the inner catheter lumen 138 as desired.

Figure 6E:
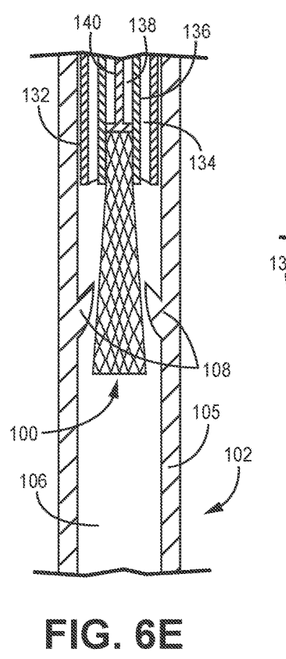
Figure 6F:
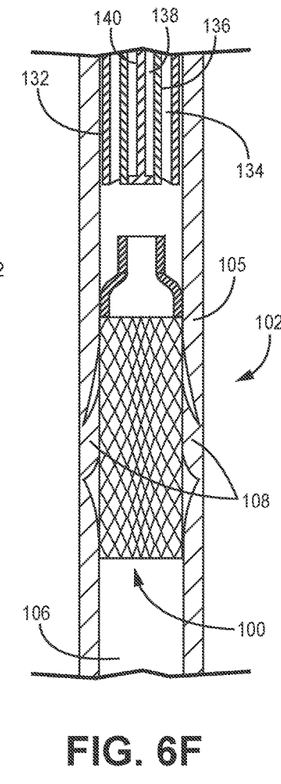

The venous valve prosthesis 100 may be released from the inner catheter lumen 138 and to the treatment site (FIGS. 6E and 6F and 760 of FIG. 7). For example, the plunger 140 may be advanced within the inner catheter lumen 138 to push the venous valve prosthesis 100 from the distal portion of the inner catheter lumen 138. For example, a clinician may control the plunger 140 to advance the plunger 140 such that the venous valve prosthesis 100 is advanced from the inner catheter 136. As the venous valve prosthesis 100 is released from a distal end of the inner catheter lumen 138, the frame 110 may expand such that it is secured against the wall 105 of the vein 102 and anchors the valve body 114 within the vein 102. Although the frame 110 is illustrated as being self-expanding (e.g., formed from a shape memory material), in other examples, the frame 110 may be expanded via a balloon or other mechanism.

Figure 6G:
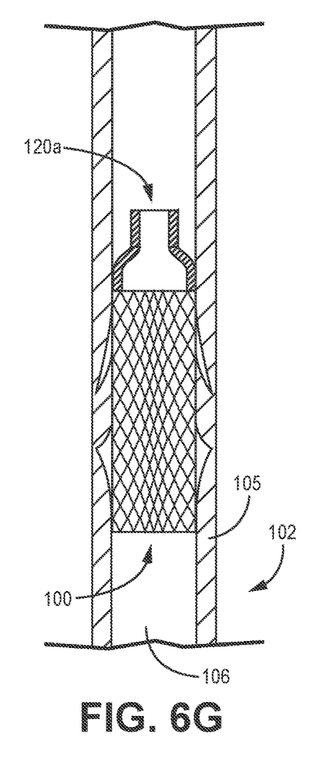

After satisfactory delivery of the venous valve prosthesis 100, the outer catheter 130, the inner catheter 134, and the plunger 138 may be removed from the vein 102 (FIG. 6G and 762 of FIG. 7).

In some examples, one or more of the guidewire 130, the outer catheter 132, the inner catheter 136, the venous valve prosthesis 100, and/or the plunger 140 may each include one or more radiopaque markers or otherwise include a radiopaque material. The radiopaque markers or other radiopaque material may facilitate implantation of the venous valve prosthesis 100 within a patient. For example, the radiopaque markers or other radiopaque material may help a clinician visualize the location of the respective component(s) with respect to the treatment site.

Due at least in part to the relative mechanical simplicity of the design of the venous valve prosthesis 100, the relative size, and the minimal components, the method used to deliver the venous valve prosthesis 100 may be simpler and less invasive than methods needed to implant other types of venous valve prostheses. For example, as discussed with respect to FIGS. 6A-6G, the venous valve prosthesis 100 may be implanted in vasculature of a patient via a percutaneous procedure, rather than via a more invasive procedure that requires a vein to be cut open in order to place the valve prosthesis 100 inside the vein.

Although an example of use of a system for delivery of the venous valve prosthesis 100 has been described, any suitable modification may be made according to particular needs, including performing the steps in a different order and/or performing more, fewer steps, and/or different steps. In some examples, the inner catheter 136 may include additional and/or different components for securing and releasing the venous valve prosthesis 100. For example, the inner catheter lumen 138 may be configured to receive a tethering device for delivering the venous valve prosthesis 100 to the treatment site. Although the system is illustrated as delivering the venous valve prosthesis 100 from a downstream direction and the venous valve prosthesis 100 is illustrated as being positioned within the inner catheter lumen 138 such that the downstream opening 120a is located at a proximal end of the venous valve prosthesis 100 as the venous valve prosthesis 100 is being delivered, the system may alternatively deliver the venous valve prosthesis 100 from an upstream direction and the venous valve prosthesis 100 may be positioned within the inner catheter lumen 138 such that the downstream opening 120a is located at a distal end of the venous valve prosthesis 100 as the venous valve prosthesis 100 is being delivered.

Although two catheters are illustrated as being used to deliver the venous valve prosthesis 100, more or fewer catheters may be used according to particular needs. For example, a single catheter may include a delivery lumen for the venous valve prosthesis 100 and a guidewire lumen for passage of the guidewire 128 and may be used to deliver the venous valve prosthesis 100 without a need for a second catheter. In some examples, a balloon or other mechanism may be used to expand the frame 110.

Although the downstream opening 120a is illustrated as being concentric with the upstream opening 120b, the stent lumen 112, and the valve lumen 118, the downstream opening 120a may, in come examples, be axially offset.

Various examples have been described. These and other examples are within the scope of the following claims.

What is claimed is:

1. An implantable medical device comprising:
a frame defining a frame lumen, the frame being expandable from a compressed configuration to an expanded configuration; and
a flexible tubular valve body extending along a longitudinal axis and between a downstream end and an upstream end, the valve body defining a valve lumen, a downstream opening at the downstream end, and an upstream opening at the upstream end, wherein the valve body is attached to the frame such that the frame lumen is in fluid communication with the valve lumen, the valve body comprising a neck, an upstream portion extending between the neck and the upstream end, and a downstream portion extending between the neck and the downstream end, the valve body being configured to fold about the neck along a direction that is transverse to the longitudinal axis, such that at least a part of the downstream portion is bent relative to at least a part of the upstream portion in a direction that is transverse to the longitudinal axis, to at least partially close the valve lumen in an absence of fluid flow through the valve lumen or in the presence of retrograde fluid flow, and the valve body configured to unfold about the neck to open in the presence of antegrade fluid flow through the valve lumen.

2. The implantable medical device of claim 1, wherein the downstream opening is smaller than the upstream opening.

3. The implantable medical device of claim 1, wherein the downstream opening is circular.

4. The implantable medical device of claim 1, wherein the downstream opening is oval.

5. The implantable medical device of claim 1, wherein the downstream portion of the valve defines at least one crease, the valve body being configured to preferentially fold along the crease to at least partially close the valve lumen.

6. The implantable medical device of claim 1, wherein the valve lumen extends between the upstream opening and the downstream opening and decreases in diameter as it extends from the upstream opening to the downstream opening.

7. The implantable medical device of claim 1, wherein a thickness of a material forming the valve body is smaller at the neck than at least at one other portion of the valve body.

8. The implantable medical device of claim 1, wherein the frame comprises steel.

9. The implantable medical device of claim 1, wherein the frame comprises nitinol.

10. The implantable medical device of claim 1, wherein the frame defines a coil.

11. The implantable medical device of claim 1, wherein the frame defines a latticed structure.

12. The implantable medical device of claim 1, wherein the frame defines an open ring.

13. The implantable medical device of claim 1, wherein the frame defines a closed ring.

14. The implantable medical device of claim 1, wherein the valve body defines a ribbed exterior surface.

15. The implantable medical device of claim 1, wherein the valve body defines a smooth exterior surface.

16. The implantable medical device of claim 1, wherein the valve body comprises a polymer or a fluoropolymer.

17. The implantable medical device of claim 1, wherein the size of the downstream opening is approximately 50%-90% the size of the upstream opening.

18. An implantable medical device comprising:
a frame defining a frame lumen, the frame being expandable from a compressed configuration to an expanded configuration; and
a flexible tubular valve body extending along a longitudinal axis and between a downstream end and an upstream end, the valve body defining a valve lumen, a downstream opening at the downstream end, and an upstream opening at the upstream end, wherein the valve body is attached to the frame such that the frame lumen is in fluid communication with the valve lumen, the valve body comprising a neck and being configured to fold about the neck along a direction that is transverse to the longitudinal axis to at least partially close the valve lumen in an absence of fluid flow through the valve lumen or in the presence of retrograde fluid flow, and the valve body configured to unfold about the neck to open in the presence of antegrade fluid flow through the valve lumen, wherein when the valve body is folded about the neck, the downstream opening faces in a first direction, and when the valve body is unfolded about the neck, the downstream opening faces in a second direction different than the first direction.

19. The implantable medical device of claim 18, wherein the frame comprises steel.

20. The implantable medical device of claim 18, wherein the frame comprises nitinol.

21. The implantable medical device of claim 18, wherein the frame defines a coil.

22. The implantable medical device of claim 18, wherein the frame defines a latticed structure.

23. The implantable medical device of claim 18, wherein the frame defines an open ring.

24. The implantable medical device of claim 18, wherein the frame defines a closed ring.

25. The implantable medical device of claim 18, wherein the valve body defines a ribbed exterior surface.

26. The implantable medical device of claim 18, wherein the valve body defines a substantially smooth exterior surface.

27. The implantable medical device of claim 18, wherein the size of the downstream opening is approximately 50%-90% the size of the upstream opening.

28. The implantable medical device of claim 18, wherein a downstream portion of the valve body defines at least one crease, the valve body being configured to preferentially fold along the crease to at least partially close the valve lumen.

29. The implantable medical device of claim 18, wherein the valve lumen decreases in diameter as it extends away from the frame.

30. The implantable medical device of claim 18, wherein a thickness of a material forming the valve body is smaller at the neck than at least at one other portion of the valve body.

31. The implantable medical device of claim 18, wherein the valve body comprises a polymer or a fluoropolymer.

32. The implantable medical device of claim 18, wherein the downstream opening is smaller than the upstream opening.

* * * * *